United States Patent
Okumura et al.

(10) Patent No.: US 7,119,900 B2
(45) Date of Patent: Oct. 10, 2006

(54) POLLEN SENSOR AND METHOD

(75) Inventors: Satoshi Okumura, Hyogo-ken (JP);
Toyohiro Usui, Hyogo-ken (JP);
Toshiaki Iwai, Hyogo-ken (JP)

(73) Assignee: Shinyei Kaisha, (JP)

( * ) Notice: Subject to any disclaimer, the term of this patent is extended or adjusted under 35 U.S.C. 154(b) by 336 days.

(21) Appl. No.: 10/678,194

(22) Filed: Oct. 2, 2003

(65) Prior Publication Data

US 2004/0066513 A1    Apr. 8, 2004

(51) Int. Cl.
*G01J 4/00* (2006.01)
(52) U.S. Cl. ..................... 356/364
(58) Field of Classification Search ............... 356/364, 356/336–339
See application file for complete search history.

(56) References Cited

U.S. PATENT DOCUMENTS

| | | | |
|---|---|---|---|
| 4,341,471 A * | 7/1982 | Hogg et al. | 356/343 |
| 4,989,978 A * | 2/1991 | Groner | 356/343 |
| 5,017,497 A * | 5/1991 | Gerard de Grooth et al. | 436/63 |
| 5,796,480 A * | 8/1998 | Igushi | 356/336 |
| 6,320,650 B1 * | 11/2001 | Fredlund et al. | 355/75 |

OTHER PUBLICATIONS

Patent Abstracts of Japan Publication No. 2001-083079 published Mar. 30, 2001 (for Application No. 11-263166 filed Sep. 17, 1999) in the name of inventor Fumio Ogawa for applicant Stanley Electric Co. Ltd.

* cited by examiner

*Primary Examiner*—Gregory J. Toatley, Jr.
*Assistant Examiner*—Isiaka O. Akanbi
(74) *Attorney, Agent, or Firm*—Anderson Kill & Olick, PC

(57) ABSTRACT

A pollen sensor and method for detecting pollen which discriminates pollen particles floating in air from other particles on a real time basis. The pollen sensor includes an illumination position for generating a light beam, a first receiver for measuring the intensity (I) or (Ip) of a light beam scattered by floating particles in a detection zone, a second receiver for measuring the intensity (Is) of a polarized light beam in a direction perpendicular to light illuminated by the light beam and means for measuring the degree of polarization of the particles for distinguishing pollen particles from other particles.

7 Claims, 7 Drawing Sheets

JAPANESE CEDAR POLLEN

POLLEN SENSOR AND METHOD

TECHNICAL FIELD

The present invention relates to a pollen sensor and method for detecting pollen particles and discriminating pollen particles floating in air from other particles on a real time basis. More specifically, the pollen sensor and method detects pollen particles floating in air which can be a cause for pollenosis.

BACKGROUND OF THE INVENTION

Conventionally, a microscope has been used to detect the number of pollen particles floating in air using a visual inspection process in which a glass plate is exposed to air for some time to collect pollen particles. The glass plate is stained, followed by a skilled technician's counting by visual inspection the stained particles through his or her microscope (hereinafter referred to as the "microscope method").

The above microscope method is a lengthy time consuming process requiring advanced skills to count the stained pollen particles by visual inspection. In addition, the microscope method does not permit pollen particles to be detected on a real time basis which is a significant drawback. The place for taking measurements using a microscope is also very limited, which is another drawback.

It is also known to detect pollen particles on a real time basis utilizing polarized light. This alternate method is disclosed in Japanese Patent No. 3113720 and in Japanese Patent Publication No. 2001-83079. The pollen detector described in Japanese Patent No. 3113720 does not require the expertise that the microscope method requires, and the measurement result can be obtained anywhere on a real time basis. Nevertheless, the quantity of pollen particles floating in air is so small that to increase the available number of pollen particles, a large volume of air should be blown into the detection zone. However, this also increases the probability of other floating particles being simultaneously passed into the detection zone. Since the pollen detector described in Japanese Patent No. 3113720 cannot discriminate pollen particles from other floating particles, the pollen detector is prone to error. Moreover, either a decrease in luminous energy emitted from the light source over time or lens contamination will reduce the intensity of the scattered light beams, making it even more difficult to discriminate pollen particles from other particles.

A similar detection device is described in Japanese Patent Publication No. 2001-83079 which is capable of measuring floating particles in real time. This device cannot discriminate pollen particles from other particles passed through the detection zone when the volume of air blown into the detection zone is increased. Accordingly, this device has the same deficiencies as the pollen sensor described in Japanese Patent No. 3113720.

OBJECTS OF THE INVENTION

It is an object of the present invention to provide a pollen sensor and method of detection capable of accurately counting the number of pollen particles floating in the air in a detection zone on a real time basis. Another object of the present invention is to provide a pollen sensor and method for accurately discriminating pollen particles from other floating particles even if the luminous energy emitted by the illumination portion is weakened over time.

SUMMARY OF THE INVENTION

The present invention is based on the discovery that the degree of polarization of scattered light beams from pollen particles is smaller than the degree of polarization from other floating particles even of the same particle size as pollen particles. This principal is used in the pollen sensor of the present invention to discriminate pollen particles from other floating particles.

The pollen sensor of the present invention comprises: an illumination portion for illuminating particles floating in air using light beams polarized in a given direction; a first receiver for selectively measuring the intensity (Ip) of a light beam from a detection zone polarized parallel to the light beam polarized in a given direction from the illumination portion with the light beam selected from a group of light beams scattered by the floating particles; a second receiver for selectively measuring the intensity (Is) of light beam from a detection zone polarized perpendicular to the light beam polarized in a given direction from the illumination portion with the light beam selected from a group of light beams scattered by the floating particles and means for discriminating pollen particles from other floating particles including means for computing the degree of polarization of such particles as an arithmetic value from the intensity (Ip) of the polarized light beam detected by the first receiver and the intensity (Is) of the polarized light beam detected by the second receiver.

In accordance with another embodiment of the present invention, the pollen sensor comprises: an illumination portion for illuminating particles floating in air using a light beam polarized in a given direction; a first receiver for measuring the intensity (I) of a light beam corresponding to the dispersion of the light beam scattered by the floating particles; a second receiver for selectively measuring the intensity (Is) of light beams polarized perpendicular to light illuminated by the illumination portion from a group of light beams scattered by the floating particles; means for discriminating pollen particles from other floating particles from the degree of polarization of such particles computed from the intensity (I) of the scattered light beam detected by the first receiver and the intensity (Is) of the polarized light beam detected by the second receiver.

When the incident light is linearly polarized (hereinafter referred to as the "incident polarizing direction"), the degree of polarization can be computed either as an arithmetic value using (Ip), which is the intensity of light polarized parallel to the incident polarizing direction and (Is) which is the intensity of light polarized in a direction perpendicular to the incident polarization direction or as an arithmetic value using (I), which is the intensity for all polarized scattered light, and (Is) which is the intensity of light polarized in a direction perpendicular to the incident polarizing direction.

More specifically, for the first embodiment the degree of polarization may be expressed by the formula $(Ip-Is)/(Ip+Is)$ wherein (Ip) is the intensity of the light beam polarized in the incident polarizing direction and (Is) is the intensity of the light beam polarized perpendicular to the incident polarizing direction. Alternatively, for the second embodiment the degree of polarization may be expressed by the formula $(I-Is)/I$ wherein (I) is the intensity for all polarized scattered light and (Is) is the intensity of a light beam polarized perpendicular to the incident polarizing direction. A comparison of the degree of polarization of the pollen particles to that of other floating particles shows that the degree of polarization for pollen particles is smaller than that of other floating particles. This characteristic permits the pollen sensor to discriminate pollen particles from other floating particles.

ADVANTAGEOUS EFFECTS OF THE INVENTION

Utilizing the pollen sensor and method of the present invention, any person can readily discriminate pollen particles from other floating particles on a real time basis and can perform a real time analysis of the pollen count. Furthermore, the present invention can discriminate pollen particles form other particles notwithstanding the amount of air blown into the detection zone or the number of floating particles passed through the detection zone.

In addition, the present invention can accurately discriminate pollen particles from other particles even though the luminous energy from a light source in the illumination portion weakens over time and/or lens contamination occurs reducing the luminous energy that reaches the detection zone. Thus, the pollen sensor and method of the present invention permits simultaneous passage of two or more floating particles with a reliable output even if there is a reduction of light volume from light source due to its life problem, or a reduction of dispersion light volume due to the dirt of a lens.

DETAILED DESCRIPTION OF THE PREFERRED EMBODIMENTS

Figure 1:
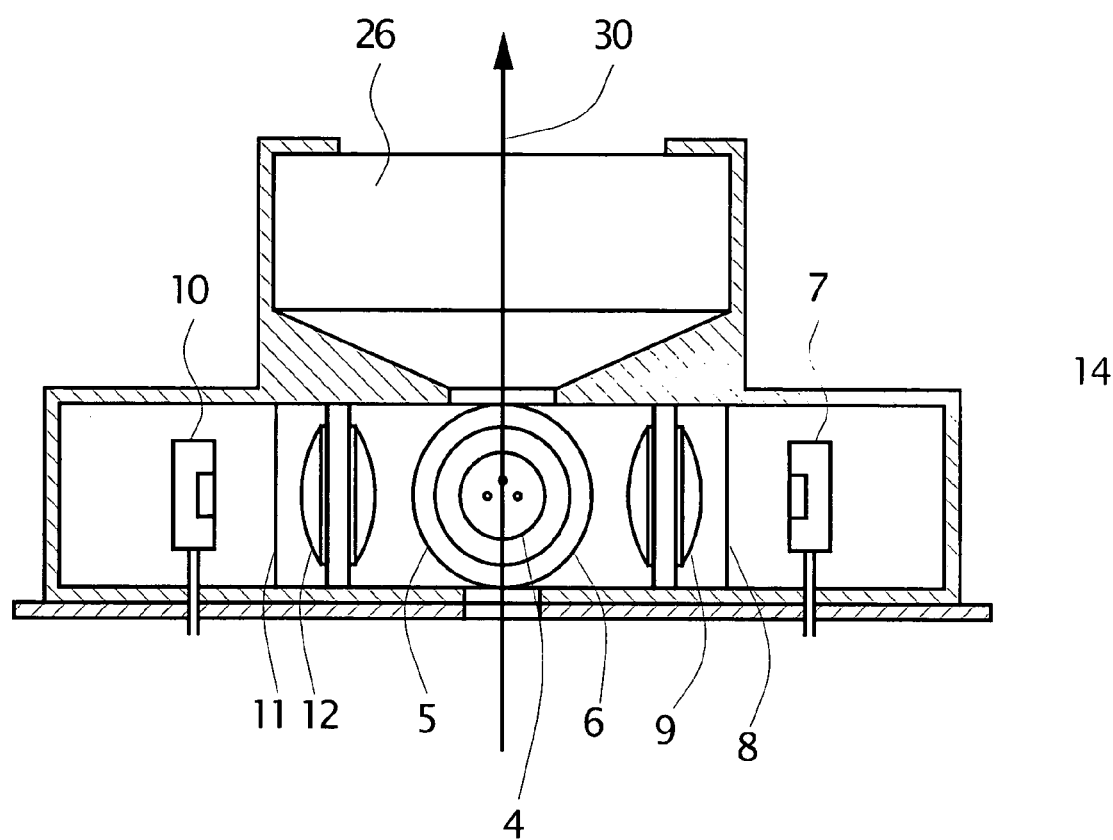
FIG. 1 is a cross-sectional view of the pollen sensor of the present invention.
Figure 2:
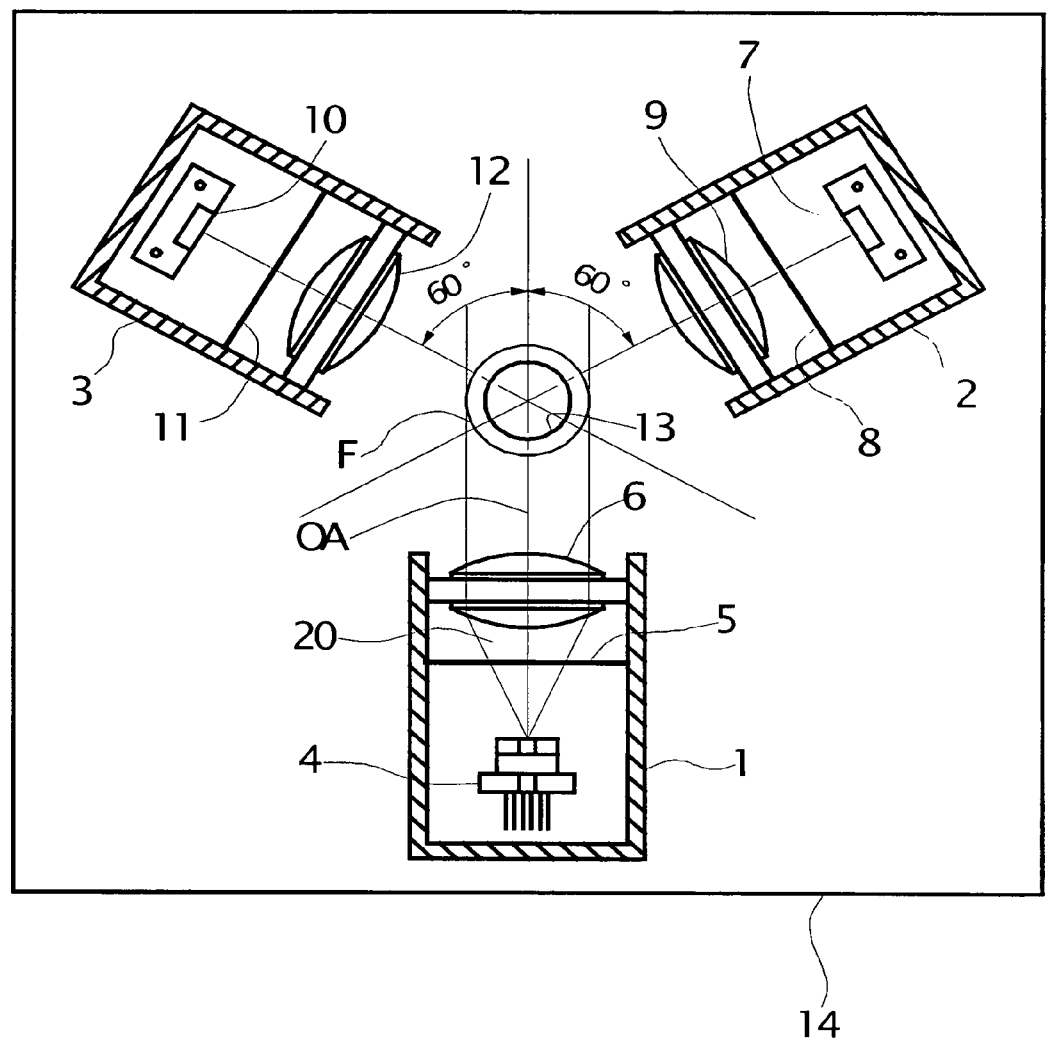
FIG. 2 is a plan view of the pollen sensor of FIG. 1, looking downwardly, part of the housing uncovered to show the arrangement of the first and second receiver to the illumination portion.
Figure 3:
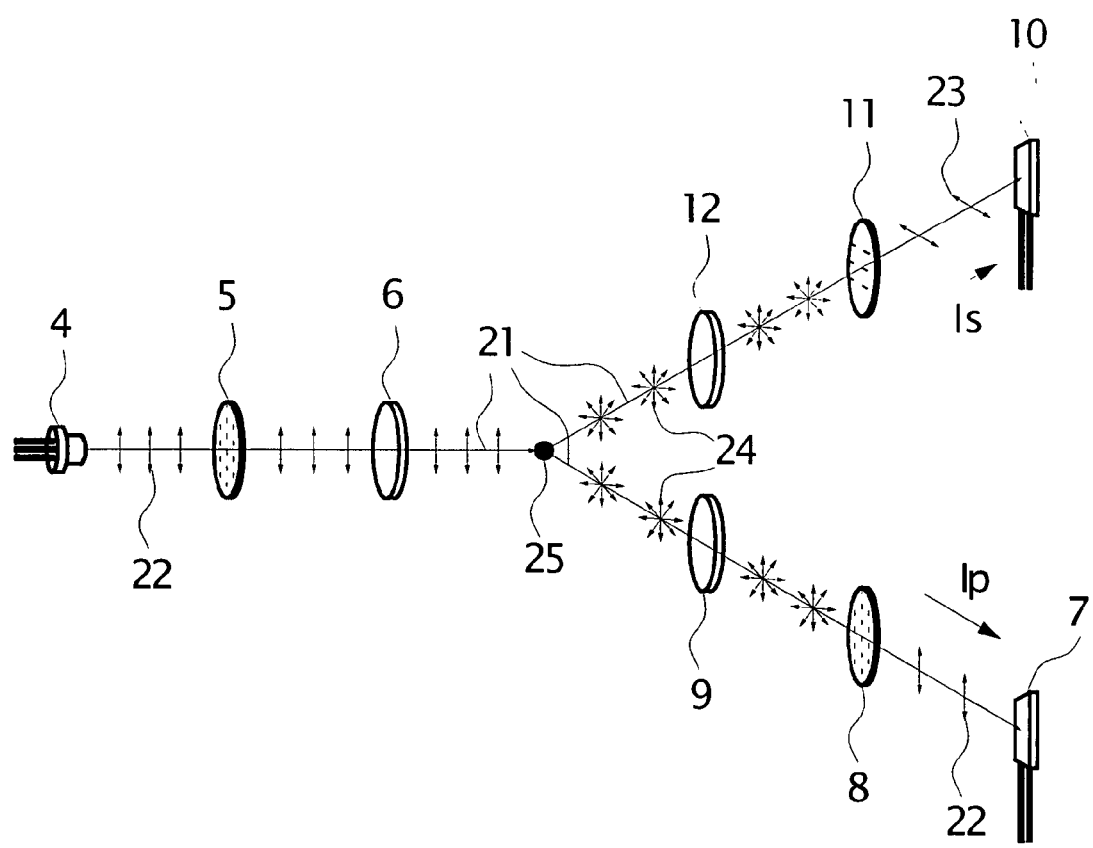
FIG. 3 is a diagrammatic view of the method of detecting the light intensity (Is) and light intensity (Ip) components of light scattered by the floating particles in accordance with the present invention.

The present invention is described hereinafter with reference to FIGS. 1–9 of the drawings. As shown in FIGS. 1 and 2, the pollen sensor of the present invention comprises a shielding housing 14 which forms a confined area for housing an illuminating portion 1 containing a light beam generating source 4, preferably a semiconductor laser diode. The light beam generating source generates a light beam 20 for illuminating one or more particles 25 (FIG. 3) floating in air within the detection zone F. The light beam 20 has a direction of polarization 22 perpendicular to the plane of the page of FIG. 2 as is diagrammatically illustrated in FIG. 3. The pollen sensor further comprises a first receiver 2 having a photodiode 7 aligned in the scattering polarizing direction of the light beam 20, preferably at 60 degrees to the incident optical axis "OA" for measuring the intensity (Ip) of light beams polarized in a direction parallel to the incident polarizing direction of light selected from a group of light beams scattered by the floating particles; a second receiver 3 having a photodiode 10 provided in the scattering polarizing direction, preferably at 60 degrees to the incident optical axis "OA", for measuring the intensity (Is) of light beams in a direction 23 which is polarized perpendicular to the light beam illuminated by the illumination portion selected from a group of light beams scattered by the floating particles and an electronic circuit 32 for discriminating pollen particles from other floating particles.

The pollen sensor also comprises an air blow port 13 located at the bottom of the shielding housing 14 to direct sampling air drawn from the atmosphere by a fan 26 through the air blow port 13 into the shielding housing 14. The sampling air is introduced into the sensor in a direction from the bottom to the top of the plane containing FIG. 2.

Any semiconductor laser diode 4 may be used such as, e.g., an RLD 65 MZT 1, manufactured by Rohm for generating the light beam 20. The laser diode 4 is contained in an illuminating portion 1 supported in the housing 14 which, as shown in FIGS. 1 and 2, also includes a polarizing filter 5 and a plastic lens 6. One example of a polarizing filter 5 is the HN 38, manufactured by Polaroid. The polarizing filter 5 has a polarizing axis in a direction perpendicular to the plane containing FIG. 2 and is perpendicular to the plastic lens 6. The plastic lens 6 has a focal length "f" of preferably 10 mm, i.e. f=10 mm. Lens 6 is arranged in the illuminating portion of the sensor in such a manner that the laser light transmitted through the polarizing filter 5 forms parallel beams of light energy upon reaching the detection zone (F). The detection zone F lies at the intersection of the light path through the filter 6 and the light path of the randomly polarized light 24 to the first and second receiver 2 and 3 respectively.

The first receiver 2 includes a polarizing filter 8 such as, e.g., HN 38, manufactured by Polaroid, a plastic lens 9 (f=10 mm) and a photodiode 7 such as, e.g., S 2506-02 manufactured by Hamamatsu Photonics for measuring light transmitted through the polarizing filter 8. The polarizing axis of the polarizing filter 8 is perpendicular to the plane containing FIG. 2 in the same manner as that of the polarizing filter 5 in the illuminating portion 1 of the pollen sensor.

The second receiver 3 includes a polarizing filter 11 such as e.g., HN 38, manufactured by Polaroid, a plastic lens 12 (f=10 mm) and a photodiode 10 such as, e.g., S 2506-02 manufactured by Hamamatsu Photonics for measuring light transmitted through the polarizing filter 11. The polarizing axis of the polarizing filter 11 is set perpendicular to the polarizing axis of polarizing filter 5, which is in parallel to the plane containing FIG. 2.

Figure 4:
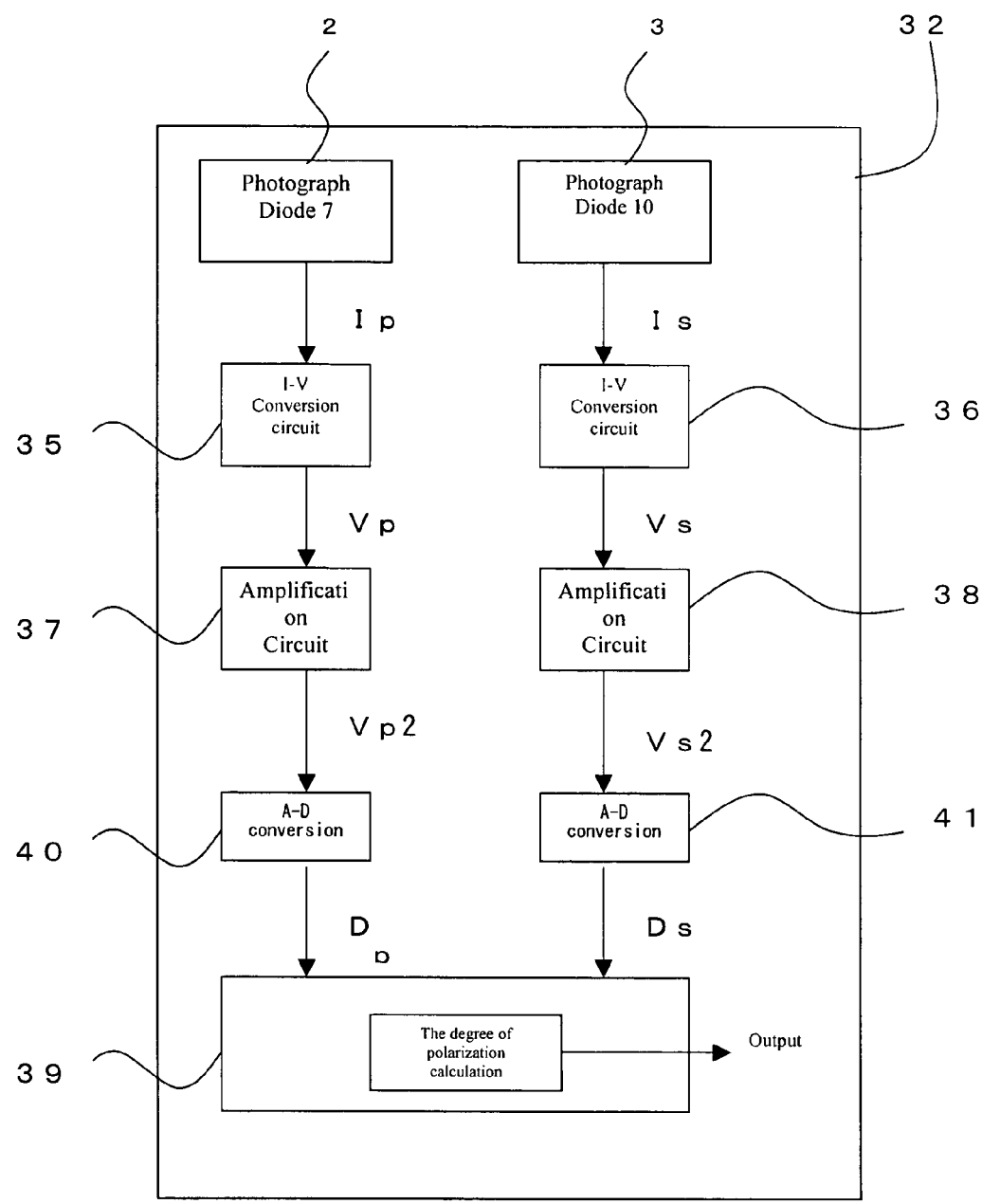
FIG. 4 is a circuit schematic block diagram of the preferred means for discriminating pollen particles from other particles in the pollen sensor of FIGS. 1 and 2 respectively.
Figure 5:
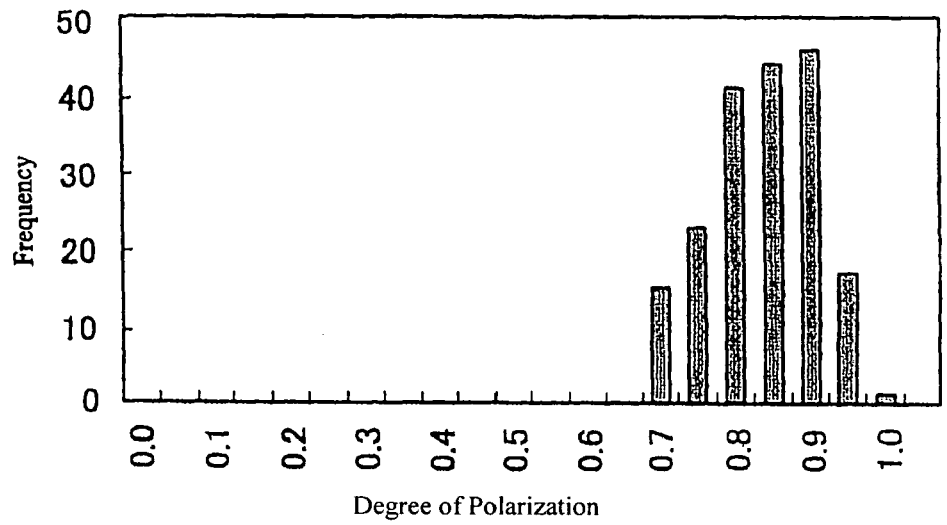
FIG. 5 is a histogram illustrating the degree of polarization of 20-micron polystyrene latex particles.
Figure 6:
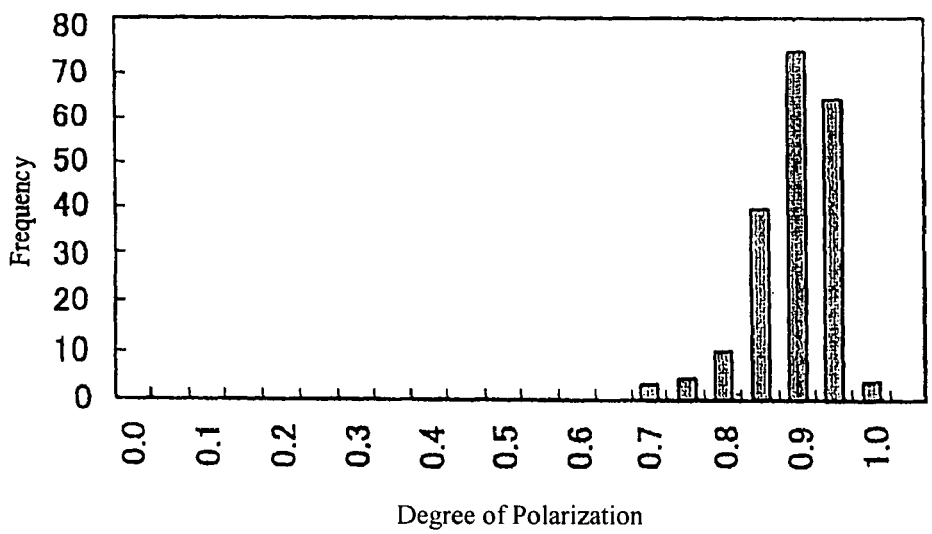
FIG. 6 is a histogram illustrating the degree of polarization of 30-micron latex particles.
Figure 7:
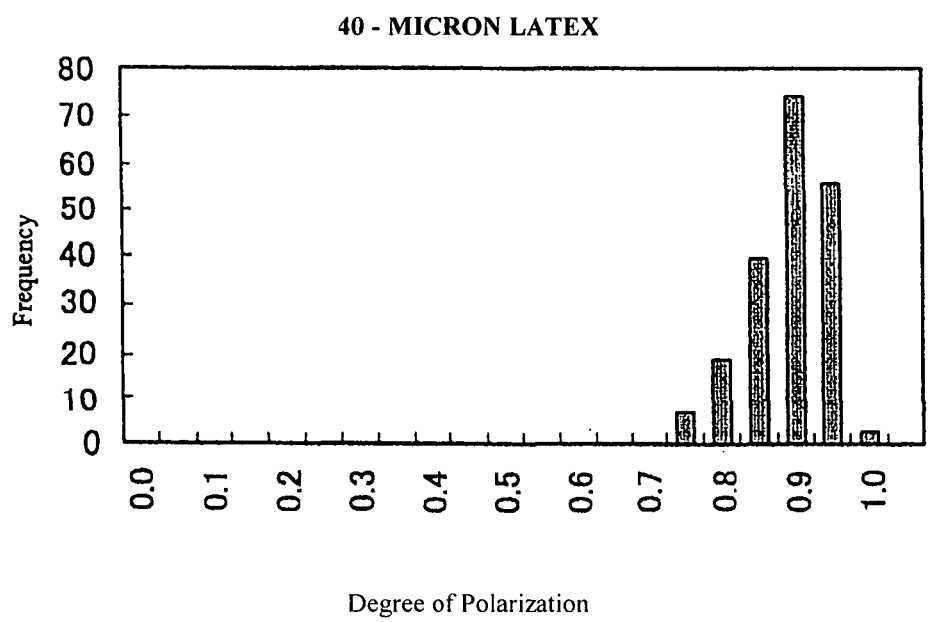
FIG. 7 is a histogram illustrating the degree of polarization of 40-micron latex particles.

As shown in FIG. 4, the photoelectric current conversion signal Ip and the photoelectric current conversion signal Is are fed to current voltage conversion circuits 35 and 36 respectively, to form voltage signals Vp and Vs respectively. The voltage signals Vp and Vs are amplified by the respective amplifiers 37 and 38 and converted into digital signals through the analog to digital converters 40 and 41 and fed into a microprocessor 39 for computing the degree of polarization as an arithmetic value utilizing (Ip), the intensity of polarized light detected by the receiver [2] and (Is), the intensity of polarized light detected by the second receiver [3] in accordance with the following formula:

$$\text{degree of polarization} = (Ip-Is)/(Ip+Is)$$

Figure 8:
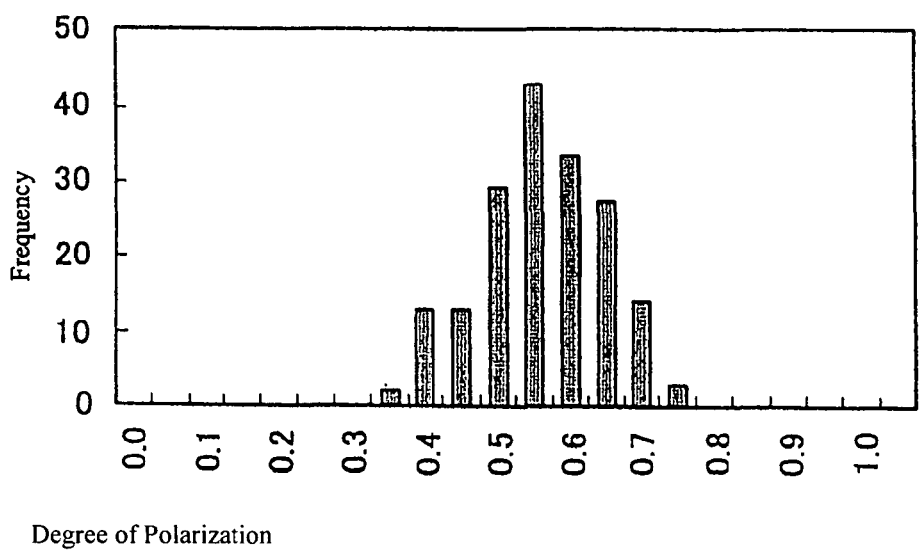
FIG. 8 is a histogram illustrating the degree of polarization of Japanese cedar pollen particles.

The computation of the degree of polarization, as defined above, permits a determination to be readily made in accordance with the present invention as to whether the detected particles constitute pollen particles or other floating particles. It has been determined that when the computation of the degree of polarization $(Ip-Is)/(Ip+Is)$ is in the range of 0.35–0.75 the detected particles constitute pollen particles. This range of 0.35–0.75 may vary with changes in the angle of alignment between the photodiode of the first and second receivers and the axis of the illuminating light beam generating portion (optical axis) which, for the preferred embodiment of the present invention, has been set at 60°. FIGS. 5–8 are histograms illustrating the comparative measurement of the degree of polarization for 20-micron polystyrene latex particles, 30-micron polystyrene latex particles, 40-micron polystyrene latex particles, and for Japanese cedar pollen particles respectively. The X-axis shows the degree of polarization (Ip Is)/(Ip+Is); and the Y-axis shows the frequency of particle detection. As is apparent from FIGS. 5–7 the range of measurement of the degree of polarization for the latex particles falls between 0.7–1.0 and for the Japanese cedar pollen particles as shown in FIG. 8 is between 0.35–0.75 permitting a possible overlap in measurement in the range between 0.70–0.75. Although some overlap in the measurement of the degree of polarization may exist between pollen particles and other floating particles, the degree of overlap consists of only about 5% of the total particle count and is therefore minimal. Thus, pollen particles are readily distinguishable from other floating particles using the pollen sensor and method of the present invention.

Figure 9:
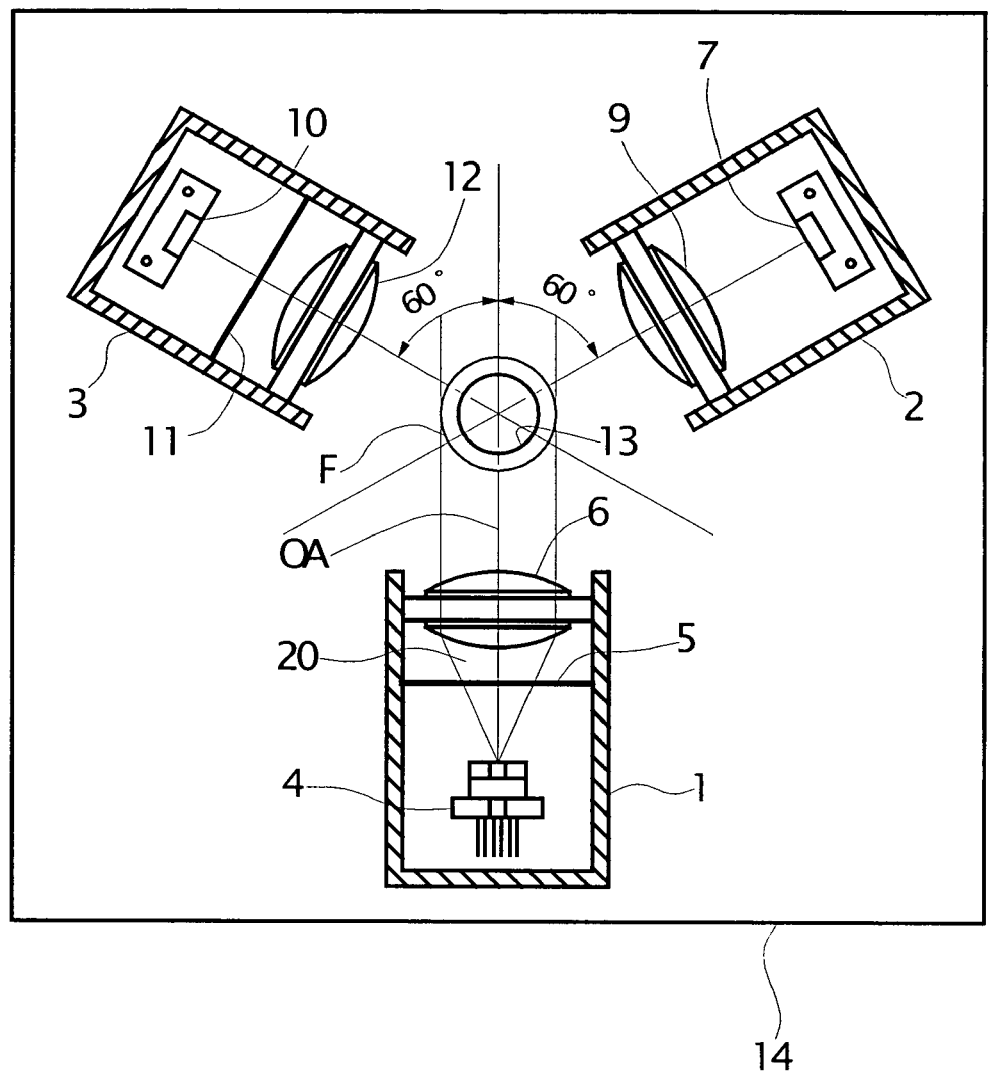
FIG. 9 is a plan view of a pollen sensor similar to that of FIG. 2, showing another embodiment of the present invention.

FIG. 9 is a plan view illustrating the configuration of another embodiment of the pollen sensor of the present invention. The pollen sensor in this embodiment excludes filter 8 from the first receiver 2 and is otherwise identical to the pollen sensor in FIG. 2. In FIG. 9, the components constituting the same elements as is shown in the sensor of FIG. 2 have the same reference symbols. In this embodiment, light beams scattered from floating particles directly reach photodiode 7 without passing through a polarizing filter. As a result, an output photoelectric conversion signal I will correspond to the intensity of the scattered light beams for all polarizing directions. Accordingly, the degree of polarization for this embodiment is computed in accordance with the formula: $(I-Is)/I$. When the degree of polarization falls within the range of 0.35–0.75, the particles constitute pollen particles as in the first embodiment and for the same reasons.

It should be understood that although the photodiode 7 in the first receiver 2 and the photodiode 10 in the second receiver 3 were each aligned in the scattering polarization direction at an angle of 60° to the incident optical axis OA, it is not essential to this invention for the angle to be limited to a 60° and, in fact, any angle within a range of 0°–90° may be used. Alternately, the scattered beams that enter a lens may be separated into a component that is in parallel to the plane containing FIG. 2 and into another component that is perpendicular to the plane containing FIG. 2, utilizing a polarized beam splitter, followed by analysis of each component using a photodiode. The degree of polarization can thus be obtained as well.

What is claimed is:
1. A pollen sensor comprising:
an illumination portion for generating a light beam having an incident optical axis for illuminating particles floating in air in a detection zone of the pollen sensor, with the light beam polarized in a given direction perpendicular to the incident optical axis;
a first receiver aligned at a first angle with respect to said incident optical axis for selectively measuring the intensity (Ip) of light beams from the detection zone polarized parallel to the light beam polarized in said given direction from said illumination portion with the light beam selected from a group of light beams scattered by said floating particles;
a second receiver aligned at a second anale spaced radially apart from the alignment axis of said first receiver to form a complementary angle of substantially equal dimension with respect to said incident optical axis for measuring the intensity (Is) of light beams from the detection zone polarized perpendicular to the light beam polarized in said given direction from the illumination portion with the light beam selected from the group of light beams scattered by the floating particles; and
means for discriminating pollen particles from other floating particles including means for computing the degree of polarization of such particles as an arithmetic value from the intensity (Ip) of the polarized light beam detected by the first receiver and the intensity (Is) of the polarized light beam detected by the second receiver.

2. The pollen sensor as set forth in claim 1, further comprising a first polarizing filter associated with said first receiver with said first polarizing filter having a polarizing axis set parallel to said incident optical axis, a second polarizing filter associated with said second receiver with said second polarizing filter having a polarizing axis set perpendicular to said incident optical axis and wherein said degree of polarization is computed in accordance with the following formula:

$$\text{degree of polarization} = (Ip-Is)/(Ip+Is)$$

wherein (Ip) is the intensity of the polarized light beam detected by the first receiver and (Is) is the intensity of the polarized light beam detected by the second receiver.

3. A pollen sensor comprising:
an illumination portion for generating a light beam having an incident optical axis for illuminating particles floating in air in a detection zone of the pollen sensor with the light beam polarized in a given direction perpendicular to the incident optical axis;
a first receiver aligned at a first angle with respect to said incident optical axis for measuring the intensity (I) of a light beam scattered by said floating particles; and
a second receiver aligned at a second angle spaced radially apart from the alignment axis of said first receiver to form a complementary angle of substantially equal dimension with respect to said incident optical axis for selectively measuring the intensity (Is) of a light beam polarized in a direction perpendicular to light illuminated by the illumination portion with the light beam selected from a group of light beams scattered by the floating particles; and
means for discriminating pollen particles from other floating particles in accordance with the degree of polarization of such particles based upon the intensity (I) of the scattered light beam detected by the first receiver and the intensity (Is) of the polarized light beam detected by the second receiver.

4. The pollen sensor as set forth in claim 3, wherein said degree of polarization is computed from the following formula:

degree of polarization $=(I-Is)/I$ wherein (I) is the intensity of the scattered light beam detected by the first receiver and (Is) is the intensity of the polarized light beam detected by the second receiver.

5. A method for detecting the presence of pollen particles floating in air in a detection zone and for discriminating between pollen particles and other particles on a real time basis comprising the steps of:

generating a light beam having an incident optical axis for illuminating particles floating in air in a detection zone with the light beam being polarized in a given direction perpendicular to the incident optical axis;

using a first receiver aligned at a first anale with respect to said incident optical axis for selectively measuring the intensity (I) or (Ip) of a light beam from the detection zone polarized parallel to the light beam polarized in said given direction from said illumination portion with the light beam selected from a group of light beams scattered by said floating particles in said detection zone;

using a second receiver aligned at a second agale spaced radially apart from the alignment axis of said first receiver to form a complementary angle of substantially equal dimension with respect to said incident optical axis for selectively measuring the intensity (Is) of a light beam from the detection zone polarized perpendicular to the light beam polarized in said given direction from said illumination portion with the light beam selected from the group of light beams scattered by the floating particles in said detection zone; and measuring the degree of polarization of such particles as an arithmetic value from the intensity (Ip) of the polarized light beam detected by the first receiver and the intensity (Is) of the polarized light beam detected by the second receiver for distinguishing between pollen particles and other particles.

6. The pollen sensor as set forth in claim 1 wherein the first and second receivers are radially spaced 60° apart.

7. The pollen sensor as set forth in claim 3 wherein the first and second receivers are radially spaced 60° apart.

* * * * *